(12) United States Patent
Hohl et al.

(10) Patent No.: US 11,651,873 B2
(45) Date of Patent: May 16, 2023

(54) THREE-DIMENSIONAL PRINTED FEEDTHROUGHS FOR IMPLANTABLE MEDICAL DEVICES

(71) Applicant: Greatbatch Ltd., Clarence, NY (US)

(72) Inventors: Brian P. Hohl, Clarence, NY (US); Dallas J. Rensel, Sanborn, NY (US); Jonathan Calamel, Clarence, NY (US); Christine A. Frysz, Orchard Park, NY (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 17/848,545

(22) Filed: Jun. 24, 2022

(65) Prior Publication Data
US 2022/0415545 A1 Dec. 29, 2022

Related U.S. Application Data

(60) Provisional application No. 63/214,942, filed on Jun. 25, 2021.

(51) Int. Cl.
| | | |
|---|---|---|
| H01B 17/30 | (2006.01) |
| B33Y 10/00 | (2015.01) |
| B33Y 80/00 | (2015.01) |
| G06F 30/10 | (2020.01) |
| B33Y 40/20 | (2020.01) |
| B28B 1/00 | (2006.01) |

(Continued)

(52) U.S. Cl.
CPC ........... *H01B 17/301* (2013.01); *B28B 1/001* (2013.01); *B33Y 10/00* (2014.12); *B33Y 40/20* (2020.01); *B33Y 80/00* (2014.12); *C04B 35/6269* (2013.01); *C04B 35/64* (2013.01); *G06F 30/10* (2020.01); *H01B 17/58* (2013.01); *H01B 19/00* (2013.01); *C04B 2235/6026* (2013.01); *G06F 2113/10* (2020.01)

(58) Field of Classification Search
CPC ....... H01F 27/04; H01F 27/02; H01B 17/265; H01B 17/301; H01B 17/26; H01B 17/00; H01B 19/00; H01B 17/56; H01B 7/00; H01B 17/30; H01B 17/28; H01R 13/53; H01R 4/70; H05K 5/03; H01H 9/02; H01H 9/0264; H01H 85/185; H02G 15/072; H01G 4/32
USPC ......... 174/142, 152 G, 153 G, 152 R, 138 R, 174/139, 138 F, 137 R, 5 R, 14 BH, 143, 174/152 GM; 16/2.1, 2.2
See application file for complete search history.

(56) References Cited

U.S. PATENT DOCUMENTS

| | | | | |
|---|---|---|---|---|
| 3,828,118 A | * | 8/1974 | Bushek | H01B 17/30 |
| | | | | 174/152 R |
| 4,678,868 A | * | 7/1987 | Kraska | H01B 17/30 |
| | | | | 174/152 GM |

(Continued)

OTHER PUBLICATIONS

"Extended European Search Report, Application No. 22181388.4, dated Oct. 31, 2022.".

*Primary Examiner* — Angel R Estrada
(74) *Attorney, Agent, or Firm* — Michael F. Scalise

(57) ABSTRACT

A ceramic subassembly manufactured by a 3D-printing process is described. The ceramic subassembly comprises a ceramic substrate having a sidewall extending to spaced apart first and second end surfaces. At least one via extends through the substrate from the ceramic substrate first end surface to the ceramic substrate second end surface. In cross-section, the via has a square-shape with rounded corners.

22 Claims, 9 Drawing Sheets

(51) Int. Cl.
  *C04B 35/626* (2006.01)
  *C04B 35/64* (2006.01)
  *H01B 17/58* (2006.01)
  *H01B 19/00* (2006.01)
  *G06F 113/10* (2020.01)

(56) References Cited

U.S. PATENT DOCUMENTS

| | | | |
|---|---|---|---|
| 8,670,829 B2* | 3/2014 | Morioka | H05K 3/4046 |
| | | | 607/37 |
| 8,978,557 B2* | 3/2015 | Hartl | F42B 3/103 |
| | | | 102/202.7 |
| 9,008,779 B2 | 4/2015 | Satou et al. | |
| 10,350,421 B2* | 7/2019 | Stevenson | H01R 13/5224 |
| 11,198,014 B2* | 12/2021 | Stevenson | H01G 2/103 |
| 2019/0344086 A1 | 11/2019 | Hammerer et al. | |

* cited by examiner

THREE-DIMENSIONAL PRINTED FEEDTHROUGHS FOR IMPLANTABLE MEDICAL DEVICES

CROSS-REFERENCE TO RELATED APPLICATION

The present application claims priority to U.S. provisional application Ser. No. 63/214,942, filed on Jun. 25, 2021.

FIELD OF THE INVENTION

The present invention generally relates to a hermetic ceramic assembly for a medical device. More specifically, the present invention relates to a 3D-printed ceramic body as a component in a hermetic assembly for use in an implantable medical device (IMD) or an active implantable medical device (AIMD). A 3D-printed ceramic body according to the present invention is first modeled on a computer. The modeled ceramic body has at least one modeled square-shaped via extending through the body. As a result of the 3D-printing and then sintering processes, however, the relatively square corners of the modeled via are transformed into rounded corners.

BACKGROUND OF THE INVENTION

Currently, manufacturing a ceramic body, such as a ceramic substrate, a ceramic feedthrough insulator, and a ceramic enclosure or housing, having at least one electrically conductive pathway requires first forming a via extending through a stand-alone ceramic body. The via is filled with an ink or paste of an electrically conductive material. This assembly is then subjected to a sintering process to complete the part.

However, a ceramic body having a complex shape or with internal features such as a high density of closely spaced vias may not even be manufacturable using current ceramic forming methods. Most ceramic parts are currently fabricated using techniques such as injection molding, tape casting, and die pressing, among others, which are limited to relatively non-complex geometries. Additionally, the absence of plasticity and ductility in commonly used ceramic materials makes drilling or machining a via hole, let alone a high density of closely spaced vias, through the ceramic difficult. Further, ceramic parts with any one or more of, for example, a highly complex geometry, an internal channel or pathway, an internal electrical feedthrough, a relatively small via, a high via count, a tight via pitch, and a via with a high aspect ratio (long and narrow or long with a small diameter) are often prohibitively difficult to drill, machine, or otherwise form in a ceramic body using current techniques.

For example, drilling a via in a ceramic body limits the via diameter to the size of the drill bit. In particular, a very small diameter via is almost impossible to drill in a ceramic body, even more so when the aspect ratio of the via is high. Due to the hardness and brittleness of ceramic materials, small size drill bits tend to break before drilling is completed. Or, if successfully drilled, the wall of the via may be riveted with defects, for example, chip outs, microcracks, even fractures of the via wall. These types of defects can propagate through the ceramic body, rendering the ceramic as scrap. Even if a drill bit survives one drilling operation, it typically must be replaced for the next drilling operation because the bit loses its sharpness and consequently, its functionality. As a drill bit is used to drill multiple holes through a ceramic, not only does it lose it sharpness, but its diameter decreases which can result in drilled vias of unacceptably reduced diameters.

Machining a ceramic part can similarly prove extremely difficult due to the hardness and brittleness of commonly used ceramic materials. Not only are cutting tools other than drill bits subject to severe wear, but defects such as fractures and cracking can be generated in the ceramic part during machining. That is in addition to the difficulty of achieving good surface quality and dimensional precision in a machined via hole.

Molding is a possible solution, but such techniques require costly fixturing and mold fixtures for complex designs do not lend themselves to easily making design modifications when needed, typically requiring brand new fixtures, which adds cost to an already expensive manufacturing method. Furthermore, depending on complexity, injection molding pressures often result in low yields due to defects associated with geometrically challenging design features. Monolithic production of a ceramic body with integral internal features may also be difficult to manufacture or may be unmanufacturable.

Many implantable medical devices (IMDs) and essentially all active implantable medical devices (AIMDs) require hermetic packaging to protect sensitive components and assemblies from contact with body fluids. As used herein, an IMD is any device that is surgically or medically introduced into the human body, either wholly or in part, with the intention of having the device remain in the body for an extended period of time. An AIMD is a special type of implantable medical device generally used for a diagnostic, therapeutic or rehabilitation purpose. An AIMD often houses sophisticated electronics or microelectronics that are designed to support or sustain human life, prevent impairment of human health, deliver medication, monitor body functions, and provide support to organs and tissues, among other functionalities. Exemplary implantable devices and systems range from gastric and cardiac pacemakers, cardioverter defibrillators, brain sensors, cochlear sensors, ocular sensors, nerve stimulators, bone stimulators or sensors, drug delivery systems, monitors, recorders, bions, microchips, microelectromechanical systems (MEMS), and bionic and digital implants.

For example, an AIMD typically houses electronic circuitry inside its housing. The RIND may also have integral parts inside the housing that can be damaged by body fluids. Exemplary integral parts include sensors, electrical conductors, electrical pathways, internal connections, hermetically sealed electrically and thermally conductive pathways, and optically transmissive pathways. Other examples include complex internal channels (such as for drug delivery), and complex internal feedthrough pathways to facilitate connection options, such as when input connections are not aligned with output connections, thereby requiring internal pathway continuity features, traces, pads, or channels.

Furthermore, the continued emphasis on miniaturization of IMDs and AIMDs magnifies packaging challenges. For example, hermetic vias tend to be a critical feature of the feedthrough for an IMD and an AIMD. When a via extending through a ceramic body is filled with an electrically conductive paste or ink and the paste or ink is then hermetically sealed to the ceramic body by sintering, design features such as ceramic part thickness, via diameter, via length, via wall surface quality, and via design complexity all become critical. Each of these parameters, either alone or in combination, can influence sustained hermeticity of the ceramic assembly and, ultimately, of the device embodying the assembly. Sustained hermeticity means that a specified helium leak rate in std cc He/sec is maintained throughout assembly, manufacturing and functional operation within a device or system structure.

Particularly notable is that there are currently no commercially available feedthrough technologies that provide external electrical contacts with spacings as small as 200 μm (0.0079 in.) to 400 μm (0.0158 in.). This means that there is no feedthrough today that is compatible with the latest miniature implantable packaging currently in development or with current integrated circuit I/O (input/output) pad spacings. For example, the latest neural interface devices being developed are reported to have electrically conductive pathway densities as high as 1,000 per $cm^2$, however, a commercially available hermetic high-density feedthrough (HDF) with that functionality is currently not available.

Further regarding device electronics, such as sensors, antennas, EMI filters, EMI filter circuit boards, integrated optical components, electronic circuits, batteries and related components, and other such functional electronics for use in an IMD or an AIMD, similar to the electrical feedthrough design challenges discussed above, electrically conductive traces, electrodes, plates, and pathways, among other design features, are becoming more complex. They often have unusual geometries, or require integration options either internal to the device or that must be integral to other device components, such as the device housing, the electrical feedthrough, or that require a flexible substrate or a wireless enablement in order to increase functionality while reducing overall device size and volume.

Accordingly, there is a need for robust, reliable, and manufacturable ceramic bodies and assemblies. Exemplary applications include, among others, a ceramic substrate for a feedthrough and a ceramic housing for a wireless communication device, both of which have an electrically conductive pathway that is hermeticity sealed to the ceramic during manufacturing and that remains hermetic over the operational life of the feedthrough or device. The present invention fulfills these needs and provides other related advantages.

SUMMARY OF THE INVENTION

Embodiments of the present invention relate to a 3D-printed ceramic body for use in an implantable medical device (IMD) or an active implantable medical device (AIMD). To build a functional ceramic body by a 3D-printing process, a design of the ceramic body is first digitally modeled by either computer aided design (CAD) or by animation software modeling. The modeled ceramic body has at least one via extending through the body. Preferably, there is more than one via, and each of the vias has a square-shape in cross-section with relatively sharp 90° corners. Each via of the digitally modeled ceramic body is pixel aligned to a pixel grid in a photolithography-based printing system. That is to ensure that each of the one or more vias of the digitally modeled ceramic body is properly arranged, organized, and accurately positioned.

The digitally modeled design is then 3D-printed to form a green ceramic body comprising the one or more vias. The 3D-printing process begins when information for the print job is digitally transferred directly from the 3D-printing software to the 3D-printer. An exemplary printer uses a ceramic-loaded liquid (slurry) that is automatically dispensed and applied to a transparent vat. A movable build platform is dipped into the slurry from above, and the ceramic material that is deposited on the build platform is then selectively exposed to ultraviolet light from below the transparent vat. By repeating this process numerous times, a three-dimensional green part is created layer by layer. After 3D-printing, the green ceramic body with one or more square-shaped vias, each via with rounded corners is subjected to thermal processing, for example, sintering to increase the rounding of the rounded corners of the square-shaped vias. The thusly processed ceramic body can then be built into a feedthrough, and the like.

Thermal processing of a 3D-printed green ceramic body may comprise a pre-sinter step to partially harden the ceramic with the via remaining unfilled. This is followed by filling the at least one via with an ink or a paste of an electrically conductive material. The electrically conductive ink or paste is then co-sintered with the ceramic body to form a hermetic co-sintered 3D-printed ceramic body with the electrically conductive material in the via being hermetically sealed to the ceramic body.

Alternatively, the square-shaped via with rounded corners of the 3D-printed green ceramic body may be filled with an electrically conductive ink or a paste directly after 3D-printing. There is no pre-sintering step. This assembly is then sintered to transform the electrically conductive ink or paste and the ceramic body into a completed hermetic co-sintered 3D-printed ceramic body.

The foregoing and additional advantages and characterizing features of the present invention will become increasingly more apparent to those of ordinary skill in the art by reference to the following detailed description and the appended drawings.

DETAILED DESCRIPTION OF THE PREFERRED EMBODIMENTS

Figure 1:
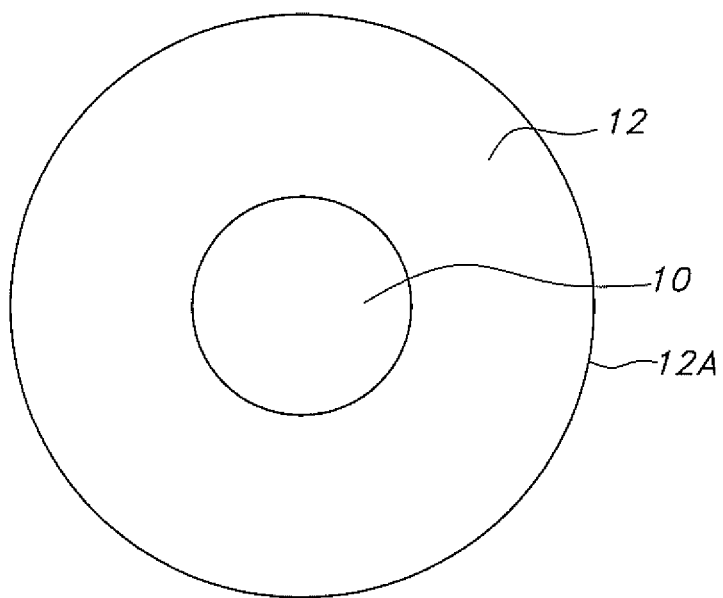
FIG. 1 is a plan view of a prior art rounded via 10 extending through a cylindrically-shaped ceramic body 12.

According to the present invention, three-dimensional (3D) printing technologies, also known as additive manufacturing (AM), are used to fabricate physical parts, such as a ceramic insulator for a feedthrough, in a discrete point-by-point, line-by-line or layer-by-layer additive manner. Additive manufacturing is defined as a manufacturing technology that creates objects through a sequential point-by-point, line-by-line or layer-by-layer stacking process.

In general, 3D-printing follows the principles of modeling, printing and finishing. Modeling is used to create a "blueprint" of the object to be 3D-printed. The modeled blueprint can be created by computer aided design (CAD) or animation modeling software.

The workflow for 3D-printing starts with designing a 3D model in CAD software. The model is then exported from the CAD software and imported into 3D-printing software. The 3D-printing software is typically unique to the manufacturer of the 3D-printer, as this allows for the best use of capabilities and features of the 3D-printer and the available materials used in that printer. After the 3D model is imported into the 3D-printing software, the print settings (resolution, size, orientation, support materials, speed, etc.), layout of the part, and material to be used are selected. Once setup is completed, the 3D-printing software generates the machine code that is then sent to the 3D-printer. The 3D-printer uses the machine code to run the printing job based on the specific print settings for a particular part. Upon completion of 3D-printing, the part is removed from the 3D-printer and subsequent processing steps, as desired, can occur.

An exemplary 3D-printing machine that is suitable for the present invention is a photo-polymerization machine. A printing process using such a machine is first created as a digitally modeled design. The 3D-printing process begins when information for the modeled design is digitally transferred directly from the design computer to the 3D-printing software and then to the 3D-printer. The exemplary photo-polymerization 3D-printer uses a ceramic-loaded liquid (slurry) that is automatically dispensed and applied to a transparent vat. A movable build platform is dipped into the ceramic slurry from above, and the ceramic material that is deposited on the build platform is then selectively exposed to ultraviolet light from below the transparent vat. By repeating this process numerous times, a three-dimensional green part is created layer by layer. After 3D-printing, the green ceramic body with square-shaped vias, each via with rounded corners is subjected to thermal processing, for example, sintering to increase the rounding of the rounded corners of the one or more square-shaped vias. The thusly processed ceramic body can then be built into a feedthrough, and the like.

A particular advantage of 3D-printing technologies is the ability to create almost any shape or geometry, simple or complex, including those with design features that are currently considered "unmanufacturable" using conventional fabrication methods such as casting, molding, drilling or machining. In the specific case of a hermetic feedthrough, 3D-printing enables the manufacture of:

very thin hermetic substrates;
geometrically complex electrical feedthrough designs;
hermetic electrical feedthroughs with complicated electrically conductive pathways;
hermetic electrical feedthroughs with thin or narrow isolation distances;
complex housings or enclosures, including those with intricate via patterns, locations, density and difficult aspect ratios;
hermetic components having extremely small via holes or via holes having high aspect ratios (i.e., relatively long via holes with relatively small diameters), high via hole counts or high via hole density, and tight pitch;
complex substrate or feedthrough configurations;
unusual substrate or feedthrough geometries; and combinations thereof.

Turning now to the drawings, FIG. 1 is a plan view, in cross-section, of a prior art cylindrically-shaped via 10 extending through a cylindrically-shaped ceramic substrate or insulator 12. Showing the insulator 12 as a cylindrical structure is exemplary. Those skilled in the art will readily understand that the outer sidewall 12A of the insulator 12 can have a myriad of shapes including rectangular with rounded corners and oval. The exact shape of the insulator 12 is dictated by the specific application in which the insulator 12 is intended to be used.

Figure 2:
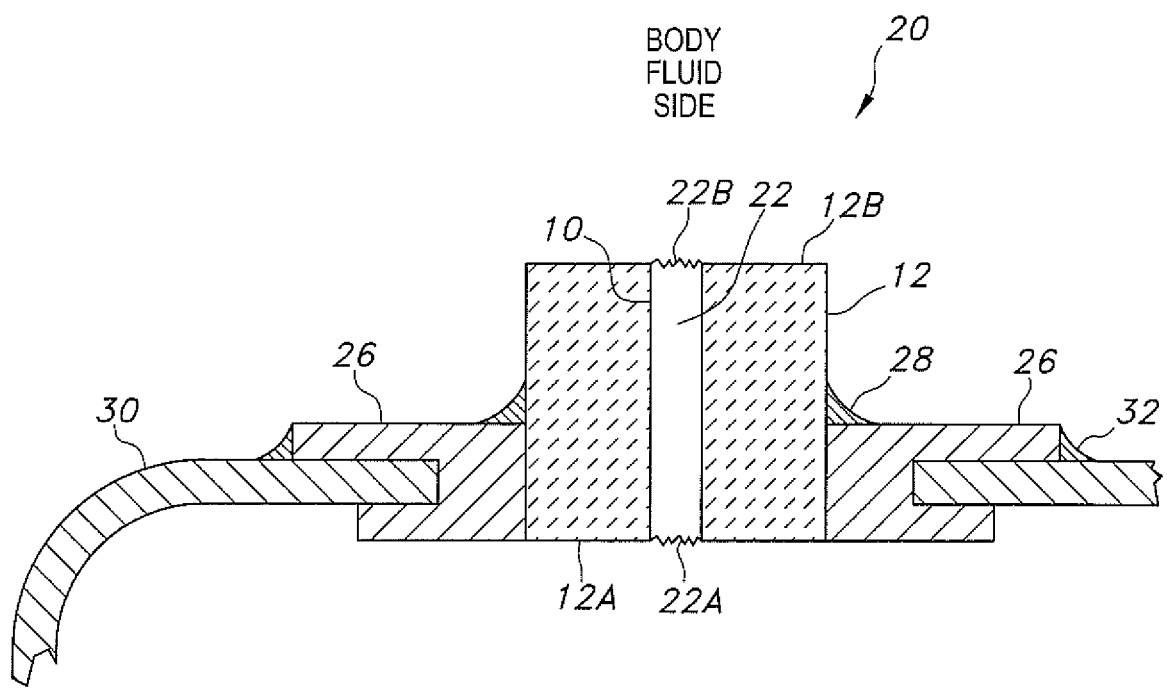
FIG. 2 is a fragmented cross-sectional view of a feedthrough 20 including the ceramic body 12 shown in FIG. 1 supporting an electrically conductive pathway 22 formed from an ink or paste that was previously filled into the via 10 in the green ceramic insulator 12, followed by sintering.

FIG. 2 illustrates an exemplary embodiment of an electrical feedthrough 20 having the via 10 extending through the ceramic insulator 12. An electrically pathway 22 extends through the insulator from a ceramic substrate or insulator first or device side end surface 12A to a ceramic substrate or insulator second or body fluid side end surface 12B. The electrically conductive pathway 22 is formed from an electrically conductive ink or paste that is filled into the via 10 with the ceramic insulator 12 in a green state. This assembly is subsequently sintered to transform the ink or paste into a solid electrically conductive pathway hermetically sealed to the sintered insulator 12.

To build an exemplary feedthrough, the insulator 12/electrically conductive pathway 22 subassembly is positioned in an opening extending through a ferrule 26. The insulator 12 is then hermetically sealed to the ferrule using a gold braze 28. That is, the outside diameter or perimeter of the insulator 12 is metalized (sputtered). The metallization is typically in two layers with a first layer being an adhesion layer and the second layer being a wetting layer (not shown). Then the ferrule is attached to these metalized ceramic layers through a gold brazing process wherein, pure gold is reflowed such that it wets the titanium ferrule and also wets to the metallized surfaces that were previously sputtered onto the ceramic insulator 12.

The resulting feedthrough assembly is secured to the housing 30 for an implantable medical device by welding 32 the ferrule 26 to the device housing. The proximal or device side end 22A of the electrically conductive pathway 22 is configured to be electrically connected to electronics, such as a circuit board, residing inside the device housing. The distal or body fluid end 22B of the electrically conductive pathway 22 is configured to be connected to a header terminal block or external lead (not shown).

Figure 3:
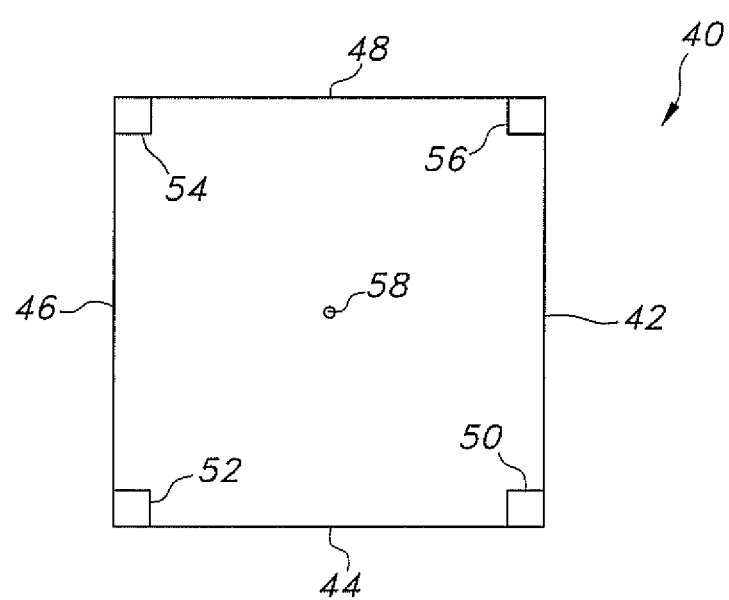
FIG. 3 is a plan view of an exemplary computer modeled square-shape via 40 with square corners prior to being printed by a 3D-printing machine.

FIG. 3 is a plan view of an exemplary square-shaped via 40 that has been modeled by a computer according to the present invention. The modeled square-shaped via 40 has four straight sidewalls 42, 44, 46 and 48 of generally equal length. Sidewalls 42 and 44 meet at a 90° corner 50, sidewalls 44 and 46 meet at a 90° corner 52, sidewalls 46 and 48 meet at a 90° corner 54, and sidewalls 48 and 42 meet at a 90° corner 56. A center point 58 of the square-shaped via 40 is equidistant to each of the sidewalls 42, 44, 46 and 48, and to each of the 90° corners 50, 52, 54 and 56.

The sharp or 90° corners of the computer modeled square-shaped via 40 are counterintuitive for a ceramic body that is intended to be built into an exemplary feedthrough for use in an IMD or an AIMD. As a point of stress concentration, a sharp corner can compromise the structural integrity of the finished ceramic part. This means that the part is more likely to fail in two ways. First, the ceramic part can fail directly from stress concentration itself, which can result in micro-cracking or visible cracks, and even catastrophic fracture and complete part failure. Second, even if the ceramic part does not succumb to cracking or fracture failure, a stress concentration feature, such as a latent crack, can dramatically shorten a product's lifecycle by weakening the part over time. Such latent failures are unpredictable and, when they occur in an IMD or an AIMD, are especially dangerous. For example, should an electrical feedthrough incorporated into an IMD or an AIMD experience a latent failure resulting in hermeticity loss, damaging body fluids can enter into the device. This can lead to complete failure of the device, which can endanger an implant patient's life.

One specific example of a life-threatening danger to an implant patient is a latent complete failure of device function for a pacemaker dependent patient. A latent hermetic failure of a cardiac pacemaker that is implanted in a pacemaker dependent patient can allow body fluid inside the device housing. This can cause failure of the enclosed microelectronic circuitry. As a result, the pacemaker may cease to electrically stimulate the pacemaker dependent patient's heart, which could be fatal. Consequently, a ceramic body that is intended for use in an IMD and an AIMD must be designed to not only provide reliable functionality, but it must also be robust enough to sustain operating functionality over the useful life of the implanted device.

Thus, even though sharp corners of the modeled square-shaped via 40 are counterintuitive in IMD and AIMD ceramic component design, they provide the following manufacturability advantages: (1) the via design enables digital modeling of a ceramic body that can be pixel aligned to a pixel grid in a photolithography-based printing system, and (2) the digital model can then be 3D-printed to form a green ceramic body having precise positional accuracy.

It is believed that corner rounding results from 3D-printing a digitally modeled square-shaped via having sharp corners that is then sintered. 3D-printing of a digitally modeled square-shaped via having sharp corners initiates a first corner rounding. The first corner rounding is believed to be due to the ceramic slurry viscosity. Corner rounding requires a high viscosity print material or medium having paste or gel-like characteristics at rest. That is so the 3D-print medium does not flow uncontrollably once dispensed into the vat.

Additionally, the 3D-print medium must rapidly transform from being fluid-like into a solid-like material after being photocured. This phase transformation (fluid-like to solid-like) is important both when spanning the via opening in the 3D-printed layer underneath the one currently being printed and when spanning the sharp corners of a via. Hence, the first rounding develops when the 3D-print medium at the 90° sharp corner overhangs the digitally defined corner so that the modeled sharp corner transforms into a rounded 3D-printed corner. Additionally, depending on the photo properties of the ceramic slurry, light absorption and scattering will affect corner rounding. Higher light scattering slurries will generate increased corner rounding.

Table 1 below provides viscosity ranges for various printing media that may be used for 3D-printing a ceramic body according to the present invention.

TABLE 1

| 3D-print medium | Viscosity range (cP) |
|---|---|
| Ink | 0.1-50,000 |
| Paste | 100,000-10,000,000,000 |
| Gel | 10,000-500,000 |

Once the ceramic body is completely 3D-printed, a sintering process is performed to remove any binder material from the ceramic and to densify the ceramic body. Shrinkage and densification cause a second rounding of the square-shaped via corners. Ceramic body shrinkage may range from 12% to 24%.

In that manner, during the 3D-printing process the square-shaped via with sharp corners 40 shown in FIG. 3 is transformed into a square-shaped via with rounded corners. The rounded corners reduce residual tangential, radial and circumferential stresses in the ceramic material adjacent to, along the length of and about the circumference of the via.

Figure 4:
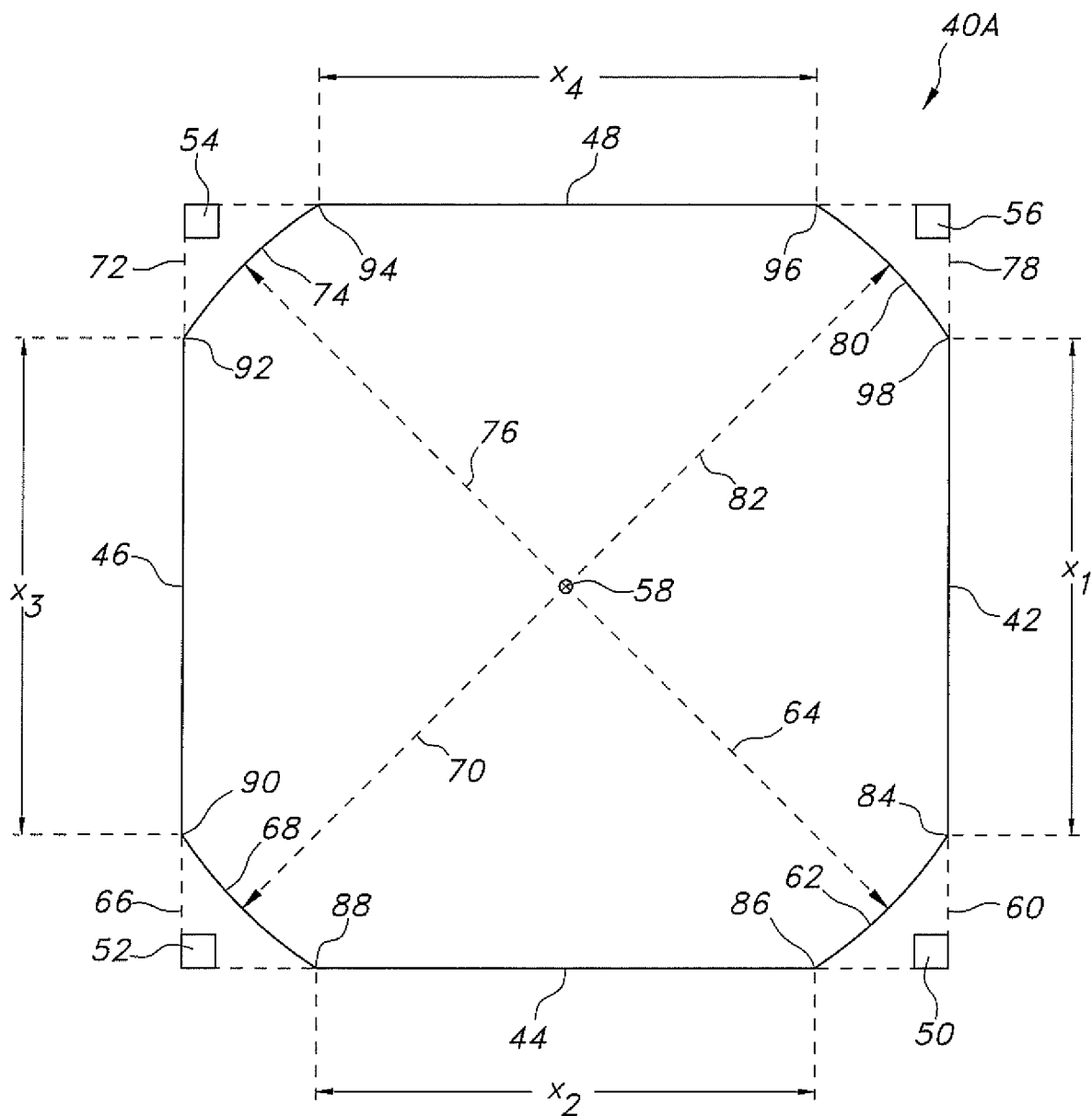
FIG. 4 is a plan view of one embodiment of the square-shape via 40A, but with the square-shaped corners shown in FIG. 3 having been rounded as a result of a 3D-printing process.

This is shown in FIG. 4, which illustrates one embodiment of a square-shaped via with rounded corners 40A according to the present invention. The 90° corner 50 of the square-shaped via 40 of FIG. 3 has been rounded as shown by the distance between the dashed line 60 indicating the original 90° corner 50 and the arc 62 of rounding 64. Likewise, 90° corner 52 has been rounded as shown by the distance between the dashed line 66 indicating the original 90° corner 52 and the arc 68 of rounding 70, 90° corner 54 has been rounded as shown by the distance between the dashed line 72 indicating the original 90° corner 54 and the arc 74 of rounding 76, and 90° corner 56 has been rounded as shown by the distance between the dashed line 78 indicating the original 90° corner 56 and the arc 80 of rounding 82. With respect to the center point 58 of the via 10, each of the radii 64, 70, 76 and 82 has substantially the same length. This means that the degree of rounding for each 90° corner 50, 52, 54 and 56 is substantially the same. The term "substantially" considers that the material forming the ceramic body through which the via 40A extends is a ceramic, which is granular and not necessarily perfectly rounded or uniformly shaped.

Looking first at arc 62, with respect to the center point 58 of the via, the degree of rounding of corner 50 is the length of the arc 62 in degrees. One end of arc 62 meets straight sidewall 42 at point 84. The other end of arc 62 meets the adjacent straight sidewall 44 at point 86. The length of arc 62 in degrees from point 84 to point 86 indicates the degree of rounding of 90° corner 50. Every point on arc 62 has substantially the same rounding 64.

Similarly, with respect to the center point 58 of the via, the degree of rounding of corner 52 is the length of the arc 68 in degrees. One end of arc 68 meets straight sidewall 44 at point 88. The other end of arc 68 meets the adjacent straight sidewall 46 at point 90. The length of arc 68 in degrees from point 88 to point 90 indicates the degree of rounding of 90° corner 52. Every point on arc 68 has substantially the same rounding 70.

With respect to the center point 58 of the via, the degree of rounding of corner 54 is the length of the arc 74 in degrees. One end of arc 74 meets straight sidewall 46 at point 92. The other end of arc 74 meets the adjacent straight sidewall 48 at point 94. The length of arc 74 in degrees from point 92 to point 94 indicates the degree of rounding of 90° corner 54. Every point on arc 74 has substantially the same rounding 76.

Finally, with respect to the center point 58 of the via, the degree of rounding of corner 56 is the length of the arc 80 in degrees. One end of arc 80 meets straight sidewall 48 at point 96. The other end of arc 80 meets the adjacent straight sidewall 42 at point 98. The length of arc 80 in degrees from point 96 to point 98 indicates the degree of rounding of 90° corner 56. Every point on arc 80 has substantially the same rounding 82.

Consequently, after rounding, the length of the remaining straight portion of sidewall 42, indicated as $x_1$, extends from point 84 to point 98, the length of the remaining straight portion of sidewall 44, indicated as $x_2$, extends from point 86 to point 88, the length of the remaining straight portion of sidewall 46, indicated as $x_3$, extends from point 90 to point 92, and the length of the remaining straight portion of sidewall 48, indicated as $x_4$, extends from point 94 to point 96.

Figure 5:
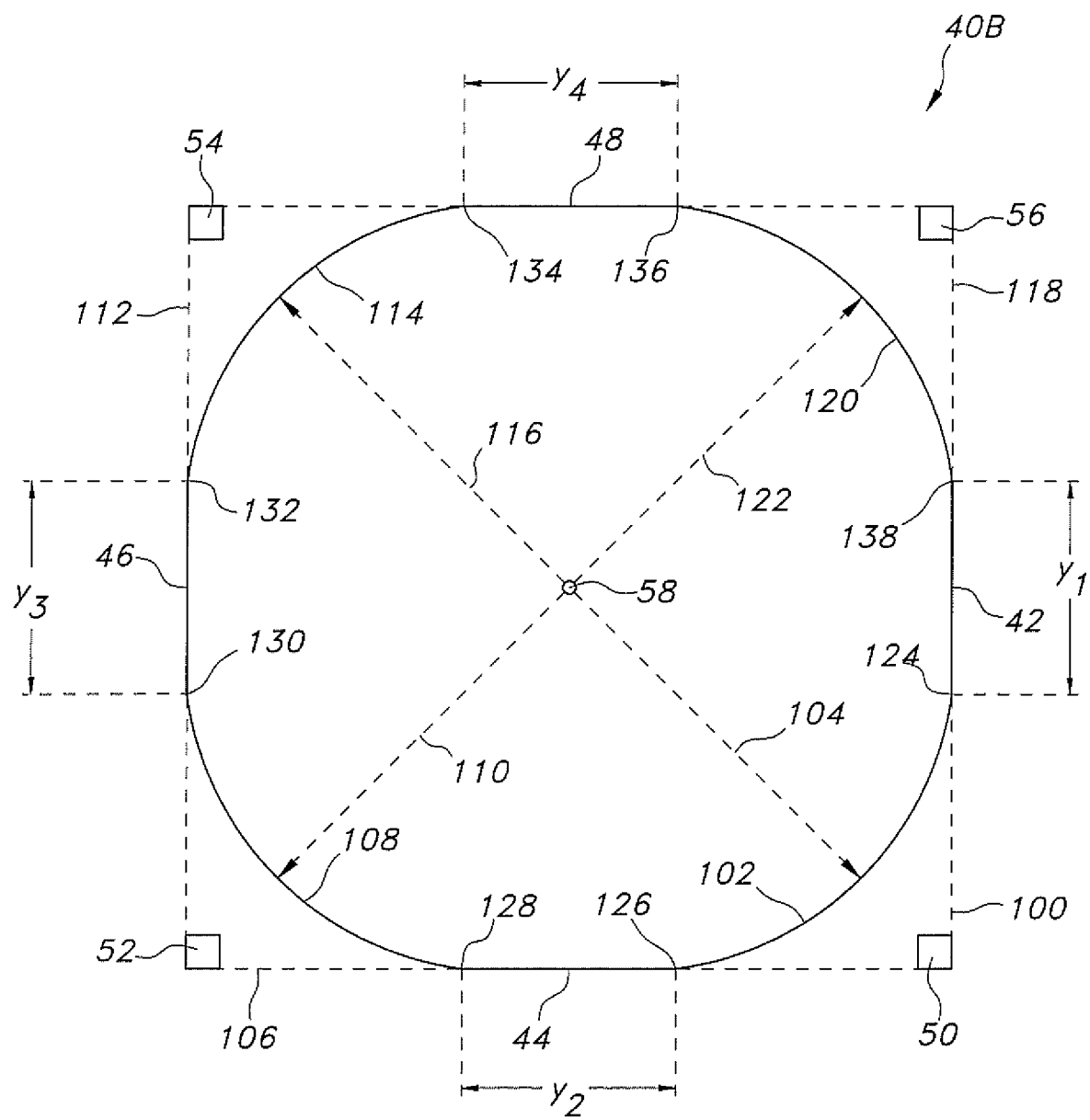
FIG. 5 is a plan view of another embodiment of a square-shape via 40B, but with the square-shaped corners shown in FIG. 3 having increased corner rounding in comparison the via 40A shown in FIG. 4.

FIG. 5 illustrates another embodiment of a square-shaped via with rounded corners 40B according to the present invention. With respect to the center point 58 of the via, the rounded corners of the square-shaped via 40B have a greater arc than those shown in FIG. 4. In particular, the 90° corner 50 of the square-shaped via 40 of FIG. 3 has been rounded as shown by the distance between the dashed line 100 indicating the original 90° corner 50 and the arc 102 of rounding 104. Likewise, 90° corner 52 has been rounded as shown by the distance between the dashed line 106 indicating the original 90° corner 52 and the arc 108 of rounding 110, 90° corner 54 has been rounded as shown by the distance between the dashed line 112 indicating the original 90° corner 54 and the arc 114 of rounding 116, and 90° corner 56 has been rounded as shown by the distance between the dashed line 118 indicating the original 90° corner 56 and the arc 120 of rounding 122. Each of the radii 104, 110, 116 and 122 has substantially the same length which means that, with respect to the center point 58 of the via, the degree of rounding for each 90° corner 50, 52, 54 and 56 is substantially the same. The term "substantially" considers that the material forming the ceramic body through which the via 40A extends is a ceramic, which is granular and not necessarily perfectly rounded or uniformly shaped.

Looking first at arc 102, with respect to the center point 58 of the via, the degree of rounding of corner 50 is the length of the arc 102 in degrees. One end of arc 102 meets straight sidewall 42 at point 124. The other end of arc 102 meets the adjacent straight sidewall 44 at point 126. The length of arc 102 in degrees from point 124 to point 126 indicates the degree of rounding of 90° corner 50. Every point on arc 102 has substantially the same rounding 104.

Similarly, with respect to the center point 58 of the via, the degree of rounding of corner 52 is the length of the arc 108 in degrees. One end of arc 108 meets straight sidewall 44 at point 128. The other end of arc 108 meets the adjacent straight sidewall 46 at point 130. The length of arc 108 in degrees from point 128 to point 130 indicates the degree of rounding of 90° corner 52. Every point on arc 108 has substantially the same rounding 110.

With respect to the center point 58 of the via, the degree of rounding of corner 54 is the length of the arc 114 in degrees. One end of arc 114 meets straight sidewall 46 at point 132. The other end of arc 114 meets the adjacent straight sidewall 48 at point 134. The length of arc 114 in degrees from point 132 to point 134 indicates the degree of rounding of 90° corner 54. Every point on arc 114 has substantially the same rounding 116.

Finally, with respect to the center point 58 of the via, the degree of rounding of corner 56 is the length of the arc 120 in degrees. One end of arc 120 meets straight sidewall 48 at point 136. The other end of arc 120 meets the adjacent straight sidewall 42 at point 138. The length of arc 120 in degrees from point 136 to point 138 indicates the degree of rounding of 90° corner 56. Every point on arc 120 has substantially the same rounding 122.

Consequently, after rounding, the length of the remaining straight portion of sidewall 42, indicated as $y_1$, extends from point 124 to point 138, the length of the remaining straight portion of sidewall 44, indicated as $y_2$, extends from point 126 to point 128, the length of the remaining straight portion of sidewall 46, indicated as $y_3$, extends from point 130 to point 132, and the length of the remaining straight portion of sidewall 48, indicated as $y_4$, extends from point 134 to point 136.

Comparing the square-shaped via with rounded corners 40A shown in FIG. 4 with the square-shaped via with rounded corners 40B of FIG. 5 illustrates that, with respect to the center point 58 of the via, as the degree of rounding of the corners 50, 52, 54 and 56 increases, the length of the remaining straight portions of sidewalls 42, 44, 46 and 48 decreases. This means that the length of sidewall portion $y_1$ is less than the length of sidewall portion $x_1$, the length of sidewall portion $y_2$ is less than the length of sidewall portion $x_2$, the length of sidewall portion $y_3$ is less than the length of sidewall portion $x_3$, and the length of sidewall portion $y_4$ is less than the length of sidewall portion $x_4$.

In other words, as the length of the straight portions of sidewalls 42, 44, 46 and 48 becomes shorter and shorter, the square-shaped via becomes progressively more rounded. And, in addition to the sintering profile of the green ceramic body, the degree of rounding is dependent on the viscosity of the printed ceramic material, the solids loading and material type of the print slurry, and the light absorption and light scattering behavior of the ceramic slurry. Each one of the variables can be modified to increase or decrease the length of a straight sidewall portion between adjacent rounded corners of an originally square-shaped via, as shown in the comparison of the square-shaped via 40A in FIG. 4 with respect to the via 40B shown in FIG. 5. For a 3D-printed via having a relatively small diameter, as corner rounding increases, the length of the straight portion of a sidewall between adjacent rounded corners decreases. With corner rounding greater than 50° up to about 70°, the originally modeled square-shaped via 40 is substantially rounded and for all intents and purposes, devoid of residual stresses attributed to a square-shaped corner.

Thus, depending on the diameter of the via, maximum residual stress in a square-shaped via with rounded corners according to the present invention occurs at about 5° to 10° corner rounding. In contrast, substantially zero residual stress occurs at about 50° to 70° corner rounding. As such, a square-shaped via with rounded corners according to the present invention has corner rounding with an arc of >10° to <90°, more preferably ≤80°. Corner rounding exceeding 90° is considered to be approaching a circle.

Suitable materials for use in a 3D-printing process to produce a hermetic substrate or feedthrough insulator according to the present invention include glasses, glass-ceramic materials and various ceramic materials. Suitable glasses include, but are not limited to, alumina borate, boro-aluminosilicate, boroaluminate, borosilicate, alumino-silicate, lanthanoborate, aluminophosphate, calcium alumi-noborate, magnesium aluminoborate, calcium magnesium aluminoborate, calcium phosphate, barium silicate, barium aluminosilicate, silicate, phosphate, borate, doped calcium phosphate, calcium phosphate with transition metal oxide additions and combinations thereof.

Suitable glass-ceramic materials include, but are not limited to, lithium disilicate, alumina lanthanoborate, titania lanthanoborate, ceramic oxide silicates, ceramic oxide borates, ceramic oxide aluminates, ceramic oxide phosphates, and combinations thereof. Suitable ceramics include, but are not limited to, alumina ($Al_2O_3$), silica ($SiO_2$), zirconia ($ZrO_2$), titania ($TiO_2$), fused silica, silicon nitride, aluminum nitride, magnesium oxide, barium oxide, barium titanate, sodium-potassium-niobate, calcium oxide, cerium oxide, apatite-wollastonite (A-W) glass ceramic, boron nitride, alumina silicate, and combinations thereof.

Other suitable ceramic materials include, but are not limited to, various stabilized or partially stabilized ceramics, various toughened ceramics, various transformation toughened ceramics, and various piezoceramic and oxide piezoceramic materials, including zirconia toughened alumina (ZTA), alumina toughened zirconia (ATZ), yttria-toughened zirconia (YTZ), yttria-stabilized zirconia (YSZ), magnesia stabilized zirconia (MSZ), hafnia stabilized zirconia, calcia stabilized zirconia, ceria stabilized zirconia, alumina stabilized zirconia, yttria stabilized tetragonal zirconia polycrystal, cesium-doped barium oxide, cesium-doped barium titanate, barium zirconate, barium titanium silicate, barium zirconate titanate, barium lanthanum cerium, transformation toughened zirconia-titania-yttria, and combinations thereof.

Suitable stabilized and toughened ceramic materials may comprise about 1 mole % to about 9 mole % of the stabilizing element. For example, a yttria-stabilized zirconia has the general formula $(ZrO_2)_{1-x}(Y_2O_3)_x$, where $0.09 \geq x \geq 0.01$. The yttria-stabilized zirconia may further comprise a 3 mole % yttria (3YSZ), a 5 mole % yttria (5YSZ), an 8 mole % yttria, a 9 mole % yttria, a 4.5 mole % yttria, or a custom mole % yttria.

A 3D-printed ceramic substrate or electrical feedthrough according to the present invention comprises a source material, which, depending on the 3D-printing process selected, may be a ceramic slurry-based material, a ceramic powder-based material or a bulk-solid based material. A non-limiting example of a 3D-printable ceramic material comprises a ceramic/polymer mixture, the polymer component being a photocurable material.

Another non-limiting example of a 3D-printable ceramic material comprises a water-based ceramic paste. Since water in the ceramic paste evaporates during the 3D-printing process, this technique eliminates the need for thermal, chemical or other means of debinding water from the ceramic material. As such, the ceramic part only needs to be thermally treated to solidify into its final form.

Still other non-limiting examples of materials that are suitable for building a 3D-printed ceramic part comprise layers of a ceramic paste that are deposited onto a build plate, powder sintering where the ceramic material is deposited in a powder form and sintered layer by layer, and binder jetting which deposits layers of binding agent on top of layers of ceramic powder, then processes the assembly to complete the part by thermal methods, such as curing, pre-sintering, co-sintering, sintering, among others.

Suitable inks and pastes for 3D-printing a part according to the present invention may have viscosities ranging from relatively low-viscosity inks to relatively high-viscosity pastes. The viscosity of the 3D-printable ink or paste increases with reduction in particle size, which helps the particles slide with respect to each other. Viscosity can be customized by solid-volume fraction loading and dispersant loading. 3D-printable inks and pastes may have relatively low to relatively high ceramic loadings. The 3D-printable ink or paste is determined by its rheological properties and rheology is customized by particle configuration and size.

In the case of a photocurable 3D-printable ink or paste, the photocurable nature of the ink or paste is dependent upon the depth to which photocuring radiation is able to penetrate the deposited ceramic material. Moreover, the photocuring behavior of a particular material can be optimized by the amount of photo-initiator that is added to the ink or paste. As an example, the addition of 2 weight % photo-initiator and 40 volume % solid loading results in the deepest curing depth for a 3D-printable ink or paste, regardless of the particle size used.

Table 2 below provides representative source material types and related 3D-printing technologies that can be used to produce ceramic parts according to the present invention, including ceramic substrates or an insulator for an electrical feedthrough.

TABLE 2

| Source Material | 3D-Printing Technology |
| --- | --- |
| slurry-based | stereolithography |
| | digital light processing |
| | two-photon polymerization |
| | inkjet printing |
| | direct ink writing |
| powder-based | three-dimensional printing |
| | selective laser sintering |
| | selective laser melting |
| | binder jetting |
| bulk solid-based | laminated object manufacturing |
| | fused deposition modeling |

A suitable protocol for 3D-printing a ceramic body having at least one via is described below:

1. Digitally Design the Ceramic Body

Prepare a digital ceramic body model having "n" number of square-shaped vias, each with sharp corners that are vertically oriented within the printable ceramic body. The term "vertically oriented" means that the via is formed vertically through the ceramic body as each ceramic layer is printed one on top of the other. Any one of the "n" number of square-shaped vias of the ceramic body may be digitally designed as a blind via, a through-via, a partial via, or combinations thereof. The "n" number of square-shaped vias of the ceramic body may further be digitally designed to be connected one to the other by a cavity, a pocket, a trough, a slit, a track, or combinations thereof, that extend between one via to a second via in any direction, orientation, trail, path or curvature.

2. Send the Machine Code to the 3D-Printer

The model is then exported from the CAD software and imported into 3D-printing software. The 3D-printing software is typically unique to the manufacturer of the 3D-printer, as this allows for the best use of capabilities and features of the 3D-printer and the available materials used in that printer. After the 3D model is imported into the 3D-printing software, the print settings (resolution, size, orientation, support materials, speed, etc.), layout of the part, and material to be used are selected. The ceramic body is digitally fit to a pixel grid so that multiple vias can be formed in alignment with the pixels of the grid of the light source used to cure the ceramic slurry. Fitting an individual via to a pixel grid results in a square-shaped via having sharp corners. Additionally, the pixels are used to size the via and to accurately locate and orient each via relative to one another (rows and columns that are angled, staggered, or random). Once setup is completed, the 3D-printing software generates the machine code that is then sent to the 3D-printer.

3. 3D-Print the Ceramic Body

The exemplary photo-polymerization 3D-printer uses a ceramic-loaded liquid (slurry) that is automatically dispensed and applied to a transparent vat. A movable build platform is dipped into the ceramic slurry from above, and the ceramic material that is deposited on the build platform is then selectively exposed to ultraviolet light from below the transparent vat. By repeating this process numerous times, a three-dimensional green part is created layer by layer. After 3D-printing, the green ceramic body with square-shaped vias, each via with rounded corners is subjected to thermal processing, for example, sintering to increase the rounding of the rounded corners of the one or more square-shaped vias.

4. Sinter the 3D-Printed Ceramic Body

The 3D-printed ceramic body may be sintered as printed. Alternatively, the vias of the 3D-printed ceramic body may be filled with an electrically conductive ink, paste or gel and this assembly is then co-sintered. Regardless, by sintering, the 3D-printed ceramic body forms a densified ceramic body as the volatiles and binders within the ceramic are thermally removed and the particles of the ceramic body sinter (which includes the particles within the via if the via is filled with an electrically conductive ink or paste prior to sintering). The combination of thermal removal of volatiles and binders and particle-to-particle sintering densifies and shrinks the ceramic body. During densification and shrinkage, the 3D-printed detail of the ceramic body also changes. Thus, densification and shrinkage results in a second rounding of the square-shaped via corners. The thusly processed ceramic body can then be built into a feedthrough, and the like.

The square-shaped via with rounded corners of a 3D-printed green ceramic body not only accurately retains the position of the via in the ceramic body, but the generally square corners are substantially rounded during the printing process, which helps further reduce tangential, radial and circumferential residual stresses in the ceramic material adjacent to, along the length of and about the circumference of the completed ceramic body. Once the 3D-printed green ceramic body with at least one square-shaped via with rounded corners is made, the green ceramic body can be filled with an electrically conductive ink or a paste, and the assembly can then be subjected to further processing, for example, sintering, to form a hermetic ceramic body.

One suitable electrically conductive ink or paste is an essentially pure platinum paste containing organic solvents and organic binders. As used herein, "essentially pure" means essentially pure post-sintering once the bulk of the binders and solvents have been baked out at elevated temperature. Once the binders and solvents have been driven out of the paste and sintering has occurred, the result is a solid pure platinum-filled via extending from the ceramic substrate or insulator first or device side end surface 12A to the ceramic substrate or insulator second or body fluid side end surface 12B of the insulator 12 shown in FIG. 2. A suitable ceramic is alumina.

Thus, the formation of an electrically conductive pathway 22 hermetically sealed to the insulator 12 in the via 10 centers around three enabling areas: (1) via packing with a high solids loading in the paste, (2) compression by the ceramic on the metal paste during binder bake out and sintering, and (3) a controlled cool down rate in combination with interfacial bonding sufficient to tolerate coefficient of thermal expansion (CTE) mismatch.

The thermal expansion of metal is generally considerably greater than those of ceramics. For example, at a bakeout temperature of 500° C., the CTE of alumina is $7.8 \times 10^{-6}$/K and of platinum is $9.6 \times 10^{-6}$/K. Historically, CTE differences within 0.5 to $1.0 \times 10^{-6}$/K between the mating metal and ceramic materials are adequate to sustain hermetic bonding between these materials. However, it is believed differences beyond these limits provided at the bake out temperature for the alumina/platinum pair may produce sufficient tensile stresses at the interface during cool down to cause spontaneous bonding failure. Hence, given the significant difference in CTEs, even at a relatively low temperature of 500° C., achieving a hermetic seal between the platinum metal and an alumina ceramic would not be expected if the difference in CTE between the sintered alumina and the platinum metal exceeds 0.5 to $1.0 \times 10^{-6}$/K. Rather, a hermetic feedthrough structure is achieved through the controlled fabrication process parameters of the platinum metal particle solids loading within the paste, controlled packing of the platinum paste within the via 10, and the controlled shrinkage of the alumina substrate 12 and platinum via paste through a prescribed co-fire heating profile.

To achieve sustainable hermeticity, the following is required: Because the CTE of platinum is sufficiently higher than the CTE of alumina, it is not theoretically possible for alumina to provide compressive forces on a platinum body in a via. Hence, to overcome the CTE differences between these two materials, the platinum body in the via must be formed using a paste, a slurry or the like, having a minimum of 80% solids loading. In a preferred embodiment, the solids loading of the platinum particles within the paste is 90%. In a more preferred embodiment, the solids loading of the platinum particles within the paste is 95%. In addition, the via must be packed with the platinum paste to occupy at least 90% of the available space within each via opening. In a preferred embodiment, the platinum paste is packed within the via opening to occupy 95% of the space. In a more preferred embodiment, the platinum paste is packed to occupy 99% of the via opening. The shrinkage of the alumina must be no greater than 20% of that of the platinum fill in the via. In a preferred embodiment, shrinkage is about 14%. In a more preferred embodiment, shrinkage is about 16%.

The green ceramic/electrically conductive ink or paste assembly is exposed to a controlled co-firing heating profile in ambient air that comprises a binder bakeout portion, a sintering portion and a cool down portion. In an embodiment, the binder bakeout portion is performed at a temperature of between 400° C. to 700° C. for a minimum of 4 hours. A preferred binder bakeout is at a temperature of between 550° C. to 650° C. A more preferred binder bakeout is at a temperature of between 500° C. to 600° C. The sintering profile portion is preferably performed at a temperature ranging from 1,400° C. to 1,900° C. for up to 6 hours. A preferred sintering profile has a temperature between 1,500° C. to 1,800° C. A more preferred sintering temperature is between 1,600° C. to 1,700° C.

The cool down portion occurs either by turning off the heating chamber and allowing the chamber to equalize to room temperature or, preferably by setting the cool down portion at a rate of up to 5° C./min from the hold temperature cooled down to about 1,000° C. At 1,000° C., the chamber is allowed to naturally equalize to room temperature. A more preferred cool down is at a rate of 1° C./min from the hold temperature to about 1,000° C. and then allowing the heating chamber to naturally equalize to room temperature. In so doing, the desired outcome of achieving a robust hermetic seal is achieved between the mating materials of the alumina insulator or substrate 12 and platinum or electrically conductive pathway 22.

During processing of the platinum fill densities and additionally during the densification phase, compression is imparted by the alumina around the platinum within the via due to the shrinkage of the alumina being greater than that of the platinum. Furthermore, the platinum is sufficiently malleable at this phase to favorably deform by the compressive forces being applied by the alumina. The combination of the platinum solids loading, the platinum packing in the via 10 and the shrinkage of the alumina being greater than the platinum fill results in the platinum taking the shape of the mating alumina surface. The amount of platinum solids loading, its packing percentage within the via 10 and the malleability of the platinum material all contribute to formation of a hermetic seal between the platinum and alumina. In addition, the compressive forces that result from the greater shrinkage of the alumina substrate 12 than that of the platinum within the via limit expansion of the platinum and force the platinum to deform such that it forms a hermetic seal. Thus, an interface between the alumina and platinum materials that conforms to the respective interface surfaces and results in a nearly exact mirror image of the interfacing surfaces is formed, thereby creating a hermetic bond therebetween. This mutually conformal interface is critical, particularly it is believed that bonding between alumina and platinum is physical.

As noted earlier, strong bonding between the alumina and the platinum is the most important factor in achieving sustainable hermeticity in feedthrough terminals for AIMDs. The co-fire parameters used to form the hermetic terminals leverage the catalytic nature of platinum, that is, platinum's affinity for certain elements, which enables either direct bonding or formation of an interfacial layer between the two materials. Analysis of the interface between the alumina and the platinum disclosed not only the creation of an intimate knitline, but, in the case of the interfacial layer, a hermetic structure that exhibits an amorphous layer at the knitline comprising the elements platinum, aluminum, carbon and oxygen that appears to impart resistance to erosion by body fluids. Both these bonding mechanisms, direct bonding and an amorphous interfacial layer, offer additional tolerance to the GTE mismatch between these two materials.

The shape of a 3D-printed green ceramic body according to the present invention is also illustrative, as a 3D-printed green ceramic body may alternatively comprise, in cross-section, a square shape, a circular shape, an octagonal shape, a tetrahedral shape, an irregular shape, a custom design or any 3D-printed green ceramic body shape that is specified or required for an application. A 3D-printed green ceramic body according to the present invention may be a rigid ceramic body or a flexible ceramic body. The 3D-printed green ceramic body may further conform to a particular shape of a bone, a tissue or an organ of an animal or a human. The 3D-printed green ceramic body according to the present invention having one or more square-shaped vias, each via with rounded corners, may comprise a ceramic substrate, an electrical feedthrough, a medical device housing or combinations thereof. The vias of the 3D-printed green ceramic body according to the present invention may be blind vias, which may provide mechanical or electrical connection to, between or among IMD or AIMD components. The vias of a 3D-printed green ceramic body according to the present invention may have hermetic electrically conductive pathways that are hermetically sealed to the ceramic body to extend from a body fluid side to a device side of an implanted medical device. The body fluid side resides outside of the implanted device (exposed to body fluids) and the device side resides inside the medical device housing where it is protected from body fluid exposure.

The hermetic electrically conductive vias of the 3D-printed green ceramic body according to the present invention may wholly comprise a single electrically conductive material, or alternatively may at least partially comprise an electrically conductive material that has two different electrically conductive materials. An electrically conductive pathway may comprise an electrically conductive metal and an electrically conductive cermet (a cermet is defined as a composite material comprising a metal and a ceramic). The electrically conductive pathway may further comprise a metal core and an electrically conductive cermet sleeve, or alternatively may comprise an electrically conductive cermet core and a metal sleeve. The electrically conductive cermet may further comprise a ceramic reinforced metal composite (CRMC).

A square-shaped via with rounded corner of the 3D-printed green ceramic body according to the present invention may alternatively be an optically transmissive pathway, alone or in combination with an electrically conductive pathway. An optically transmissive pathway may wholly comprise an optically transmissive material, or alternatively may at least partially comprise an optically transmissive material. An optically transmissive pathway may comprise an optically transmissive material core and an electrically conductive material sleeve, or alternatively may comprise an electrically conductive material core and an optically transmissive material sleeve.

Figure 6A:
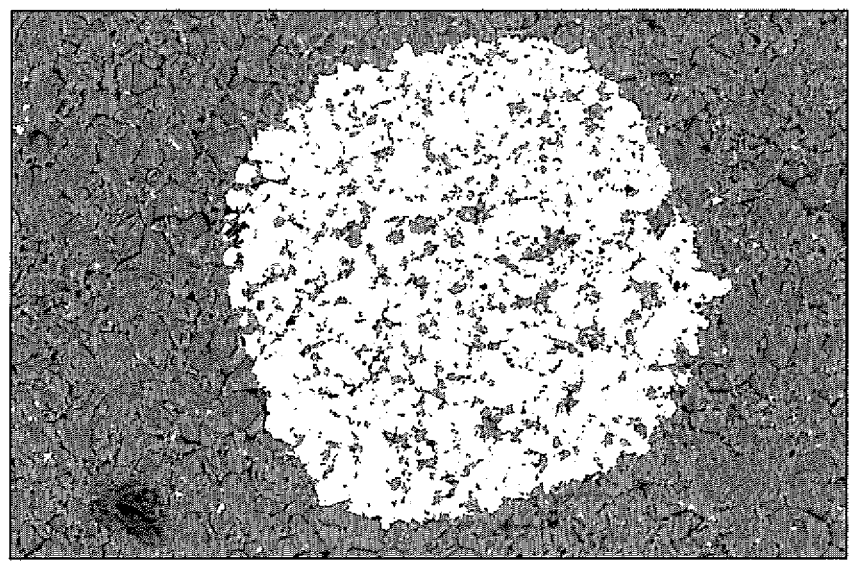
FIG. 6A is an SEM image of a co-sintered 3D-printed ceramic body with an electrically conductive paste-filled square-shaped via with rounded corners according to the present invention.
Figure 6B:
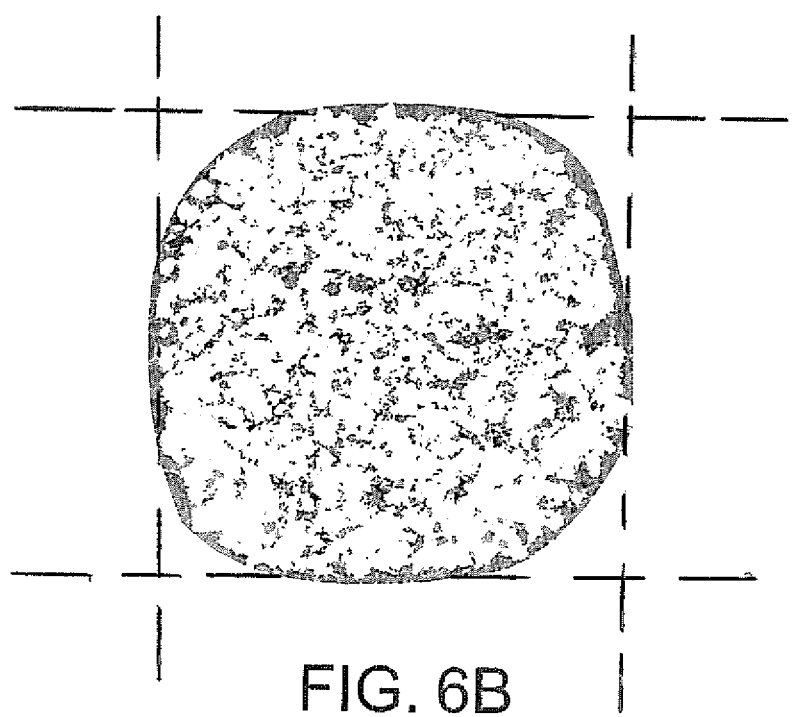
FIG. 6B shows the same SEM image of the electrically conductive paste-filled square-shaped via with rounded corners of FIG. 6A with the ceramic body having been partially cut away, but with the straight side portions of the via indicated with dashed lines.

FIG. 6 is a SEM image of a square-shaped via with rounded corners according to the present invention that has been filled with an electrically conductive paste. The paste filled via was then co-sintered with the 3D-printed green ceramic body. The 3D-printed ceramic body with the square-shaped via was made from a digital model where the square-shaped via was pixel aligned with a pixel grid so that the digital via has a square shape with 90° corners. The ceramic body of FIG. 6 was then made by a photo-polymerization-based 3D-printing process. Inspection of FIG. 6 discloses substantial rounding of the rounded corners of the square-shaped via, thereby forming a square-shaped via with rounded corners.

Thus, rounding of the modeled corners of a square-shaped via minimizes residual tensile stress about the perimeter of the via. This is reflected in that the square-shaped via rounded corners shown in FIG. 6 does not exhibit any cracking of the ceramic surrounding the co-sintered electrically conductive material in the via. Additionally, the square-shaped via with rounded corners is devoid of any separation segments about the circumference of the co-sintered electrically conductive material at and along its interface with ceramic body.

Figure 7A:
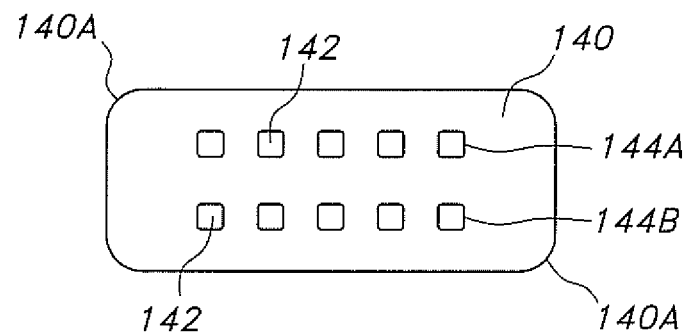
FIG. 7A is a schematic illustration of a 3D-printed green ceramic body 140 having a plurality of square-shaped vias 142, each with rounded corners, with the vias being in an inline configuration in both an x-direction and a y-direction.

In the embodiment shown in FIG. 7A, the 3D-printed green ceramic body 140 has a rectangular shape with rounded corners 140A. A plurality of square-shaped vias 142, each with rounded corners extend through the ceramic body 140. The plurality of square-shaped vias 142, each with rounded corners, are aligned in two rows 144A and 144B with the vias being in an inline configuration in both an x-direction and a y-direction. While only two rows of vias 142 are shown, there may be "n" number of vias 142 aligned in both the x- and y-directions or as rows and columns.

Figure 7B:
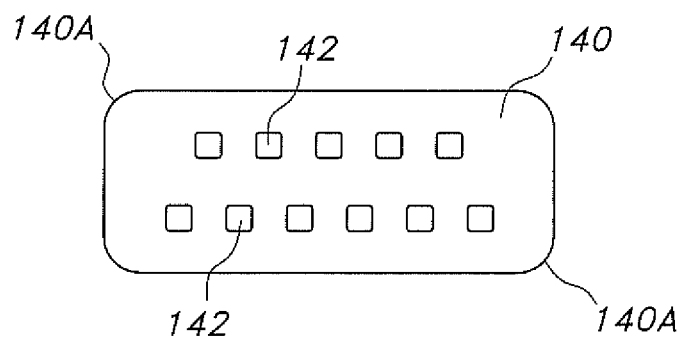
FIG. 7B is a schematic illustration of a 3D-printed ceramic body 140 having a plurality of square-shaped vies 142, each with rounded corners, aligned in the x-direction, but staggered in the y-direction.

The embodiment shown in FIG. 7B also has two rows of 3D-printed square-shaped vias 142, each with rounded corners, extending through the ceramic body 140. However, the plurality of square-shaped vias 142, each with rounded corners, are aligned in the x-direction, but staggered in the y-direction. According to the present invention, there may be "n" number of staggered via rows.

Figure 8A:
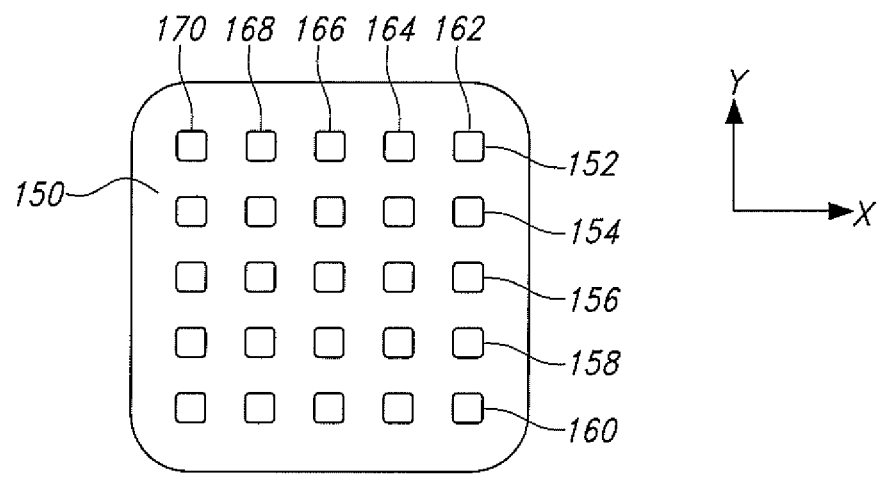
FIGS. 8A and 8B are schematic illustrations of 3D-printed green ceramic bodies according to the present invention comprising various arrays of square-shaped vias, each with rounded corners.
Figure 8B:
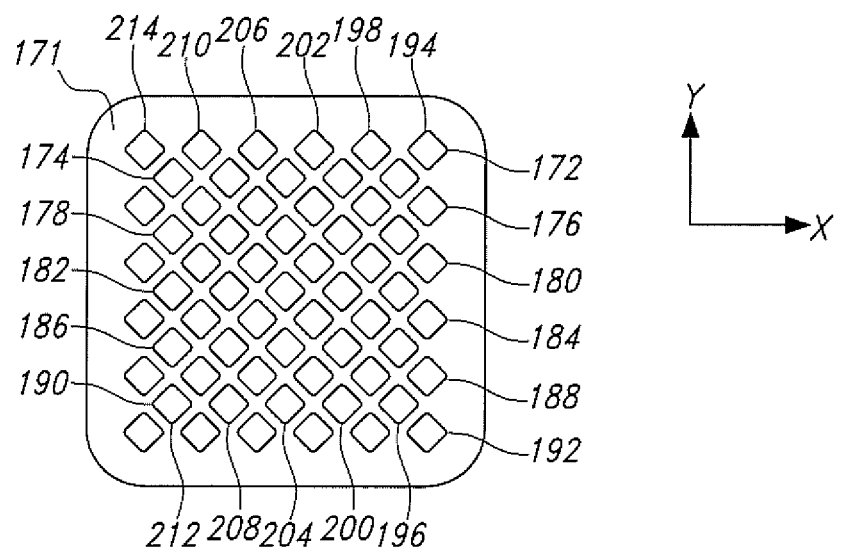

FIGS. 8A and 8B are illustrative 3D-printed green ceramic bodies according to the present invention comprising various arrays of square-shaped vias, each with rounded corners. The 3D-printed ceramic body 150 illustrated in FIG. 8A has a configuration of five inline rows of vias 152, 154, 156, 158 and 160 in the x-direction and five inline columns of vias 162, 164, 166, 168 and 170 in the y-direction. In contrast, 3D-printed ceramic body 171 illustrated in FIG. BB has an array configuration of eleven staggered rows of vias 172, 174, 176, 178, 180, 182, 184, 186, 188, 190 and 192 in the x-direction and eleven staggered columns of vias 194, 196, 198, 200, 202, 204, 206, 208, 210, 212 and 214 in the y-direction.

The arrays in FIGS. 8A and 8B each have a via packing density that is defined by the number of vias per unit area of the ceramic body. Via packing density is calculated using the following equation:

$$\eta = (A_{via} * n) / A_{ceramic}$$

where:
  η=via packing density
  $A_{ceramic}$=area of the ceramic body surface to which the via extends
  $A_{via}$=area of the via end surface
  n=number of vias in the ceramic body Percent via packing density (%η) is calculated by multiplying the via packing density η (calculated using the above equation) by 100.

Inspection of FIGS. 8A and 8B illustrates that the array shown in FIG. 8B has a via packing density that is greater than that shown in FIG. BA.

In addition to the respective via arrays, FIGS. 8A and 8B illustrate via isolation distance, which is defined as the separation distance about the perimeter of a first via relative to an immediately adjacent second via. Via-to-via isolation distance defines a controlled arrangement and ordered positioning of vias. Isolation distance can be interpreted as organized by via rows. Each via row is separated by a strut of the ceramic body, the strut comprising a defined width. In addition to via position and order, the controlled arrangement of struts enables improved mechanical properties, influences shrinkage, affects insulation resistance, alters the behavior of light, modifies magnetic energy and light fields, among others.

FIG. 8A illustrates a relatively wider strut width in the five inline rows of vias 152, 154, 156, 158 and 160 in the x-direction and the five inline columns of vias 162, 164, 166, 168 and 170 in the y-direction in comparison to the eleven staggered rows of vias 172, 174, 176, 178, 180, 182, 184, 186, 188, 190 and 192 in the x-direction and the eleven staggered columns of vias 194, 196, 198, 200, 202, 204, 206, 208, 210, 212 and 214 in the y-direction illustrated in FIG. 8B. The struts shown in FIG. 8A are aligned in the x-direction and the y-direction between two adjacent via rows, which provides an inline via row arrangement. The struts shown in FIG. 8B are aligned at a 45° angle with respect to the x- and y-directions, which provides a staggered via row arrangement.

It is important to note that via packing density (the number of vias per unit area) is also influenced by the width and orientation of the struts. In the exemplary embodiment illustrated in FIG. 8B, the thinner struts of the ceramic body, in addition to the strut orientation, effects a staggered configuration that provides a higher via density than the embodiment illustrated in FIG. 8A, which has thicker struts and an inline configuration.

Additionally, the defined width of the x-direction and the y-direction struts between the via rows in both FIGS. 8A and 8B are illustrated as being the same throughout the ceramic body in each design; however, it is anticipated that strut widths between adjacent rows may be different depending on the desired result. For example, strut widths in one design may be the same to achieve a minimum insulation resistance between electrically conductive vias while strut widths may alternatively comprise one or more different widths to alter an electrically conductive pathway field or a light transmission field. Similarly, the vias may be filled with the same ink or paste, or the ink and paste compositions may vary from via to via or from groups of vias to groups of vias to influence an electrically conductive pathway field or a light transmission field or to provide a unique function for one or more via pathways or one or more groups of via pathways. The 3D-printed green ceramic bodied according to the present invention thus offers unique design flexibility depending on the functional or use intent.

Figure 9:
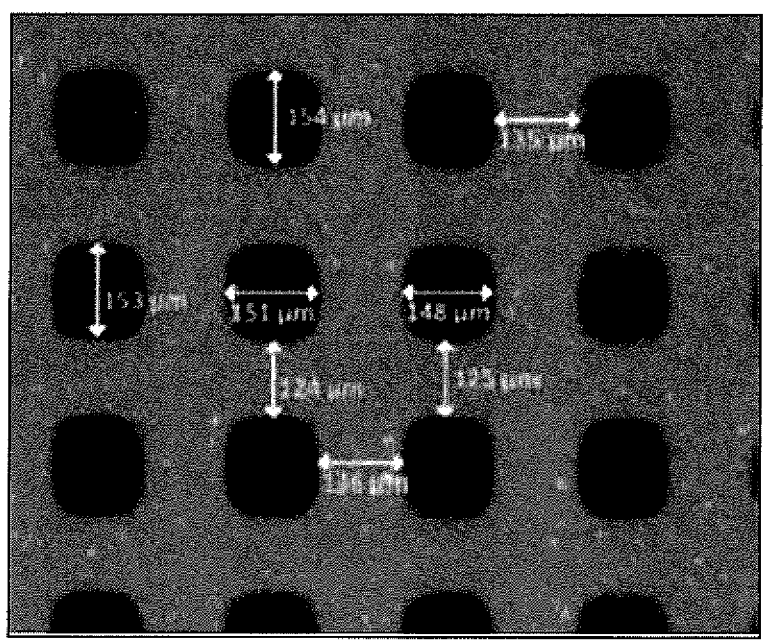
FIG. 9 is an SEM image of an exemplary 3D-printed ceramic body according to the present invention with dimensions of the vias and struts provided on the image.

FIG. 9 is an SEM image of a portion of an exemplary 3D-printed ceramic body according to the present invention. Dimensions of the vias and struts of the 3D-printed ceramic body in its green state are provided on the image. The ceramic body shown was formed using a photo-polymerization-based 3D-printing process. First, a digital CAD model with its pixels aligned to a pixel grid was created. The digital CAD model has an array of square-shaped vias, each with rounded corners arranged in an inline via row and column configuration. The parameters for this particular digital model are transferred to a 3D-printer from the CAD program and 3D-printing software. A ceramic-loaded slurry is then automatically dosed and coated on top of a transparent vat. A movable building platform is dipped into the ceramic slurry, which is then selectively exposed to ultraviolet (UV) light from below the vat. A layer image is generated by means of a digital micromirror device coupled with a projection system. This process is repeated, layer-by-layer, to form a 3D-printed green ceramic body. The 3D-printed green ceramic body is then ready for thermal post-processing to remove the binder during sintering, which results in a completed ceramic body.

A 3D-printed green ceramic according to the present invention is capable of forming vies within ±3 μm (±0.0001 in.) of a desired diameter with isolation distances within ±1 μm (±0.00004 in.) of a desired distance. More importantly, the 3D-printed ceramic body shown in FIG. 9 demonstrates that the present 3D-printing process can produce an array of vias with diameters as small as about 148 μm and with isolation distances between two adjacent vias as short or as close to each other as about 100 μm, thereby enabling the manufacture of previously unmanufacturable components that are suitable for use in an IMD and an AIMD.

More particularly, as noted earlier, the lack of electrical feedthrough technologies capable of providing external electrical contacts for connection to components, assemblies or devices comprising spacings as small as 200 µm (0.0079 in.) to 400 µm (0.0158 in.), and which are useful in miniature implantable packaging and integrated circuit I/O (input/output) applications, can now be provided by the 3D-printed ceramic body of the present invention.

Figure 10A:
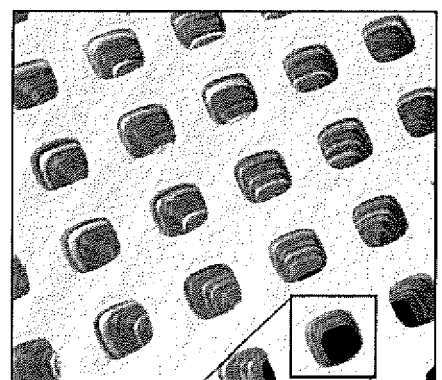
FIGS. 10A to 10C are computed tomography (CT) scan images of a portion of a ceramic body manufactured by a photo-polymerization-based 3D-printing process according to the present invention.
Figure 10B:
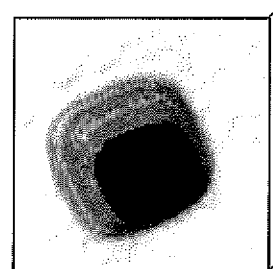
Figure 10C:
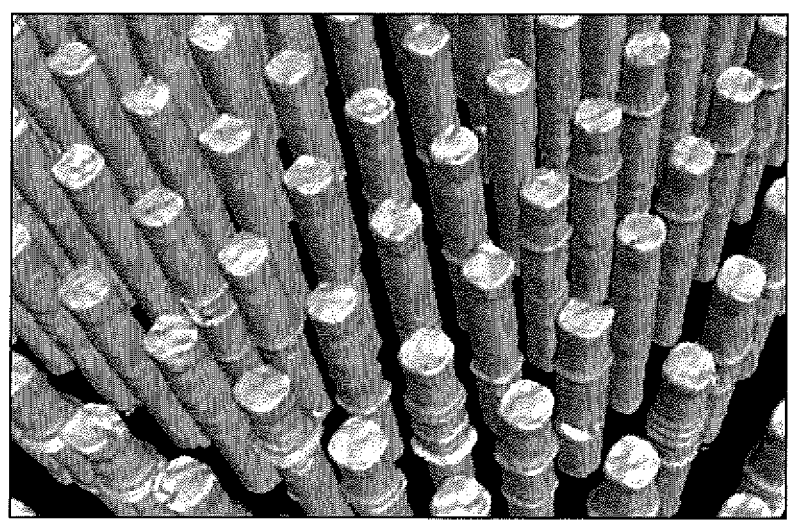

FIGS. 10A to 10C are computed tomography (CT) scan images of a portion of a ceramic body manufactured by a photo-polymerization-based 3D-printing process according to the present invention. The image of FIG. 10A shows a portion of an array of unfilled vias where each via has a square shape with rounded corners. Inspection of the square-shaped vias, each with rounded corners shows a layered appearance along the length of the via walls.

FIG. 103 is a magnified view of one of the square-shaped vias, showing in more detail the rounded corners between adjacent straight sidewalls. The layered appearance of the via wall is due to the layer-by-layer 3D-printing process used to make the ceramic body.

Additionally, this particular ceramic body comprises 200 square-shaped vias, each with rounded corners having an inline via arrangement about the surface of the 3D-printed green ceramic body. More particularly, the 3D-printed green ceramic body illustrated in FIG. 8A has a 10×10 via count, where 10 rows of square-shaped vias, each with rounded corners are arranged inline along an x-direction and 10 columns of square-shaped vias, each with rounded corners are arranged inline along a y-direction of the 3D-printed green ceramic body. The 3D-printed green ceramic body shown in FIG. 8A further has an xy-surface plane arrangement comprising a 10×10 via count of square-shaped vias, each with rounded corners aligned in an inline via array forming a 3D-printed green ceramic body comprising a 200 via count.

The CT scan image of FIG. 10C was obtained after via filling and co-sintering of the green ceramic body to form a hermetic 3D-printed co-sintered filled-via ceramic body. FIG. 10C shows only the filled-via material of the co-sintered via-filled ceramic body. Inspection of the perimeter along the length of the co-sintered filled-via material shows a similarly layered appearance essentially conformal to the corresponding layered appearance of the via wall of the 3D-printed green ceramic body.

Thus, a co-sintered 3D-printed via-filled ceramic body according to the present invention has one or more square-shaped vias, each with rounded corners having a 50 µm minimum sidewall length. The 3D-printed ceramic body of the present invention further has a 100 µm minimum isolation distance. The 3D-printing process according to the present invention enables the manufacture of ceramic bodies with via packing densities as high as or even greater than 1,000 vias per cm$^2$, making available manufacturable high-density feedthrough for use in IMDs and AIMDs, among other applications.

It is appreciated that various modifications to the inventive concepts described herein may be apparent to those of ordinary skill in the art without departing from the scope of the present invention as defined by the appended claims.

What is claimed is:

1. A ceramic subassembly, comprising:
    a) a ceramic substrate having a sidewall extending to spaced apart ceramic substrate first and second end surfaces; and
    b) at least one via extending through the ceramic substrate from the ceramic substrate first end surface to the ceramic substrate second end surface,
    c) wherein, in cross-section looking downwardly at one of the ceramic substrate first and second end surfaces and with respect to a center point of the via, the at least one via has a square-shape with rounded corners and comprises four straight sidewall portions and four rounded corners, and wherein each of the four straight sidewall portions extends to and meets with two of the rounded corners and each of the four rounded corners has an arc that ranges from about 50° to ≤80°.

2. The ceramic subassembly of claim 1, wherein the arcs of each of the four rounded corners have a similar degree.

3. The ceramic subassembly of claim 1, wherein each of the straight sidewall portions has a minimum length of about 50 µm.

4. The ceramic subassembly of claim 1, wherein the arc of each of the four rounded corners ranges from about 50° to about than 70°.

5. The ceramic subassembly of claim 1, wherein there are at least two vias extending through the ceramic substrate from the first end surface to the second end surface, and wherein the at least two vias are spaced apart from each other by a distance of at least 100 µm.

6. The ceramic subassembly of claim 1, wherein the at least one via has a diameter of about 148 µm, or greater.

7. The ceramic subassembly of claim 1, wherein an electrically conductive pathway resides in the at least one via.

8. The ceramic subassembly of claim 7, wherein the electrically conductive pathway extends to or adjacent to the first end surface and to or adjacent to the second end surface of the ceramic substrate.

9. The ceramic subassembly of claim 1, wherein the ceramic substrate is selected from alumina borate, boro-aluminosilicate, boroaluminate, borosilicate, aluminosilicate, lanthanoborate, aluminophosphate, calcium aluminoborate, magnesium aluminoborate, calcium magnesium aluminoborate, calcium phosphate, barium silicate, barium aluminosilicate, silicate, phosphate, borate, doped calcium phosphate, calcium phosphate, lithium disilicate, alumina lanthanoborate, titania lanthanoborate, ceramic oxide silicates, ceramic oxide borates, ceramic oxide aluminates, ceramic oxide phosphates, alumina ($Al_2O_3$), silica ($SiO_2$), zirconia ($ZrO_2$), titania ($TiO_2$), fused silica, silicon nitride, aluminum nitride, magnesium oxide, barium oxide, barium titanate, sodium-potassium-niobate, calcium oxide, cerium oxide, apatite-wollastonite (A-W) glass ceramic, boron nitride, alumina silicate, zirconia toughened alumina (ZTA), alumina toughened zirconia (ATZ), yttria-toughened zirconia (YTZ), yttria-stabilized zirconia (YSZ), magnesia stabilized zirconia (MSZ), hafnia stabilized zirconia, calcia stabilized zirconia, ceria stabilized zirconia, alumina stabilized zirconia, yttria stabilized tetragonal zirconia polycrystal, cesium-doped barium oxide, cesium-doped barium titanate, barium zirconate, barium titanium silicate, barium zirconate titanate, barium lanthanum cerium, transformation toughened zirconia-titania-yttria, yttria-stabilized zirconia having the general formula $(ZrO_2)_{1-x}(Y_2O_3)_x$, where $0.09 \geq x \geq 0.01$, and combinations thereof.

10. A hermetic feedthrough, comprising:
    a) an electrically conductive ferrule comprising a ferrule opening, wherein the ferrule is configured to be attachable to an opening in a housing of an active implantable medical device;

b) a ceramic substrate having an outer sidewall extending to spaced apart ceramic substrate first and second end surfaces, wherein the ceramic substrate resides in the ferrule opening where a gold braze hermetically seals the ceramic substrate outer sidewall to the ferrule;

c) at least one via extending through the ceramic substrate from the ceramic substrate first end surface to the ceramic substrate second end surface, wherein, in cross-section looking downwardly at one of the ceramic substrate first and second end surfaces and with respect to a center point of the via, the at least one via has a square-shape with rounded corners and comprises four straight sidewall portions and four rounded corners, and wherein each of the four straight sidewall portions extends to and meets with two of the rounded corners and each of the four rounded corners has an arc that ranges from about 50° to ≤80°; and d) an electrically conductive pathway extending through the via from ceramic substrate first end surface to the ceramic substrate second end surface.

11. The hermetic feedthrough of claim 10, wherein the arcs of each of the four rounded corners have a similar degree.

12. The hermetic feedthrough of claim 10, wherein each of the straight sidewall portions has a minimum length of about 50 μm.

13. The hermetic feedthrough of claim 10, wherein the arc of each of the four rounded corners ranges from about 50° to about 70°.

14. The hermetic feedthrough of claim 10, wherein there are at least two vias extending through the ceramic substrate from the first end surface to the second end surface, and wherein the at least two vias are spaced apart from each other by a distance of at least 100 μm.

15. The hermetic feedthrough of claim 10, wherein the at least one via has a diameter of about 148 μm, or greater.

16. The hermetic feedthrough of claim 10, wherein an electrically conductive pathway resides in the at least one via.

17. The hermetic feedthrough of claim 16, wherein the electrically conductive pathway extends to or adjacent to the first end surface and to or adjacent to the second end surface of the ceramic substrate.

18. The hermetic feedthrough of claim 10, wherein the ceramic substrate is selected from alumina borate, boroaluminosilicate, boroaluminate, borosilicate, aluminosilicate, lanthanoborate, aluminophosphate, calcium aluminoborate, magnesium aluminoborate, calcium magnesium aluminoborate, calcium phosphate, barium silicate, barium aluminosilicate, silicate, phosphate, borate, doped calcium phosphate, calcium phosphate, lithium disilicate, alumina lanthanoborate, titania lanthanoborate, ceramic oxide silicates, ceramic oxide borates, ceramic oxide aluminates, ceramic oxide phosphates, alumina ($Al_2O_3$), silica ($SiO_2$), zirconia ($ZrO_2$), titania ($TiO_2$), fused silica, silicon nitride, aluminum nitride, magnesium oxide, barium oxide, barium titanate, sodium-potassium-niobate, calcium oxide, cerium oxide, apatite-wollastonite (A-W) glass ceramic, boron nitride, alumina silicate, zirconia toughened alumina (ZTA), alumina toughened zirconia (ATZ), yttria-toughened zirconia (YTZ), yttria-stabilized zirconia (YSZ), magnesia stabilized zirconia (MSZ), hafnia stabilized zirconia, calcia stabilized zirconia, cerin stabilized zirconia, alumina stabilized zirconia, yttria stabilized tetragonal zirconia polycrystal, cesium-doped barium oxide, cesium-doped barium titanate, barium zirconate, barium titanium silicate, barium zirconate titanate, barium lanthanum cerium, transformation toughened zirconia-titania-yttria, yttria-stabilized zirconia having the general formula $(ZrO_2)_{1-x}(Y_2O_3)_x$, where $0.09 \geq x \geq 0.01$, and combinations thereof.

19. A ceramic subassembly, comprising:
a) an alumina substrate having a sidewall extending to spaced apart alumina substrate first and second end surfaces; and
b) at least one via extending through the alumina substrate from the alumina substrate first end surface to the alumina substrate second end surface,
c) wherein, in cross-section looking downwardly at one of the alumina substrate first and second end surfaces and with respect to a center point of the via, the at least one via has four straight sidewall portions, each of a minimum length of about 50 μm, and four rounded corners, and wherein each of the four straight sidewall portions extends to and meets with two of the rounded corners and each of the four rounded corners ranges from about 50° to ≤80°.

20. The ceramic subassembly of claim 19, wherein there are at least two vias extending through the alumina substrate from the first end surface to the second end surface, and wherein the at least two vias are spaced apart from each other by a distance of at least 100 μm.

21. The ceramic subassembly of claim 19, wherein the at least one via has a diameter of about 148 μm, or greater.

22. The ceramic subassembly of claim 19, wherein an electrically conductive pathway resides in the at least one via.

* * * * *